(12) United States Patent
Raab et al.

(10) Patent No.: US 8,808,251 B2
(45) Date of Patent: Aug. 19, 2014

(54) DRIVE ASSEMBLY AND MEDICATION DELIVERY DEVICE

(75) Inventors: Steffen Raab, Frankfurt am Main (DE); Ulrich Brüggemann, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 667 days.

(21) Appl. No.: 13/143,040

(22) PCT Filed: Jan. 19, 2010

(86) PCT No.: PCT/EP2010/050554
§ 371 (c)(1),
(2), (4) Date: Sep. 26, 2011

(87) PCT Pub. No.: WO2010/084109
PCT Pub. Date: Jul. 29, 2010

(65) Prior Publication Data
US 2012/0010576 A1   Jan. 12, 2012

(30) Foreign Application Priority Data
Jan. 20, 2009  (EP) ..................................... 09000686

(51) Int. Cl.
*A61M 5/00* (2006.01)
*A61M 5/315* (2006.01)
*A61M 5/30* (2006.01)
*A61M 5/24* (2006.01)
*A61M 5/20* (2006.01)

(52) U.S. Cl.
CPC ......... *A61M 5/31585* (2013.01); *A61M 5/3157* (2013.01); *A61M 5/30* (2013.01); *A61M 5/24* (2013.01); *A61M 5/31593* (2013.01); *A61M 5/31568* (2013.01); *A61M 5/20* (2013.01)
USPC ........................................ 604/211; 604/232

(58) Field of Classification Search
CPC .............. A61M 5/24; A61M 5/31553; A61M 5/31585; A61M 5/31583; A61M 5/31551; A61M 5/31555; A61M 5/3158; A61M 5/3155; A61M 5/31578; A61M 5/31525; A61M 5/31533; A61M 5/31581; A61M 5/31586; A61M 5/31528; A61M 5/31568; A61M 5/31593; A61M 5/20; A61M 5/30; A61M 5/3157
USPC .................. 604/207–211, 218, 224, 232, 246
See application file for complete search history.

(56) References Cited

U.S. PATENT DOCUMENTS 5,092,842 A * 3/1992 Bechtold et al. ............... 604/135
5,104,380 A * 4/1992 Holman et al. ................ 604/117

(Continued)

FOREIGN PATENT DOCUMENTS

| DE | 102004063650 | 7/2006 |
|----|--------------|--------|
| EP | 0338806 | 10/1989 |
| EP | 1353712 | 10/2003 |

OTHER PUBLICATIONS

International Preliminary Report on Patentability and Written Opinion for International Patent Application. No. PCT/EP2010/050554, dated Jul. 26, 2011.

(Continued)

*Primary Examiner* — Kevin C Sirmons
*Assistant Examiner* — William Carpenter
(74) *Attorney, Agent, or Firm* — McDonnell Boehnen Hulbert & Berghoff LLP

(57) ABSTRACT

A drive assembly suitable for a medication delivery device comprises a housing, a drive member, a piston rod, a rotation sleeve, a guide member and a biasing member. The rotation sleeve is arranged to be displaced in a distal direction when the drive member is displaced in the distal direction by mechanical interaction of the drive member and the rotation sleeve with the rotation sleeve and the drive member both being guided axially by the at guide member. The biasing member exerts a force on the rotation sleeve acting in the proximal direction, said force being transformed into a rotational movement of the rotation sleeve. The rotational movement of the rotation sleeve being transformed into a rotational movement of the piston rod.

15 Claims, 5 Drawing Sheets

(56) References Cited

U.S. PATENT DOCUMENTS

| | | | |
|---|---|---|---|
| 5,626,566 A * | 5/1997 | Petersen et al. | 604/208 |
| 5,921,966 A * | 7/1999 | Bendek et al. | 604/207 |
| 6,019,747 A * | 2/2000 | McPhee | 604/211 |
| 6,048,336 A * | 4/2000 | Gabriel | 604/211 |
| 6,241,709 B1 * | 6/2001 | Bechtold et al. | 604/207 |
| 6,899,699 B2 * | 5/2005 | Enggaard | 604/246 |
| 7,195,616 B2 * | 3/2007 | Diller et al. | 604/224 |
| 7,749,186 B2 * | 7/2010 | Kohlbrenner et al. | 604/67 |
| 7,811,263 B2 * | 10/2010 | Burren et al. | 604/211 |
| 7,850,662 B2 * | 12/2010 | Veasey et al. | 604/207 |
| 7,857,791 B2 * | 12/2010 | Jacobs et al. | 604/224 |
| 7,951,113 B2 * | 5/2011 | Kohlbrenner et al. | 604/135 |
| 8,083,711 B2 * | 12/2011 | Enggaard | 604/68 |
| 8,409,148 B2 * | 4/2013 | Fiechter et al. | 604/197 |
| 8,672,898 B2 * | 3/2014 | Enggaard | 604/211 |
| 2002/0120235 A1 | 8/2002 | Enggaard | |
| 2006/0153693 A1 | 7/2006 | Fiechter et al. | |

OTHER PUBLICATIONS

European Search Report for EP App No. 09000686, dated Jun. 3, 2009.

International Search Report for Int. Patent App. No. PCT/EP2010/050554, mailed Feb. 23, 2010.

* cited by examiner

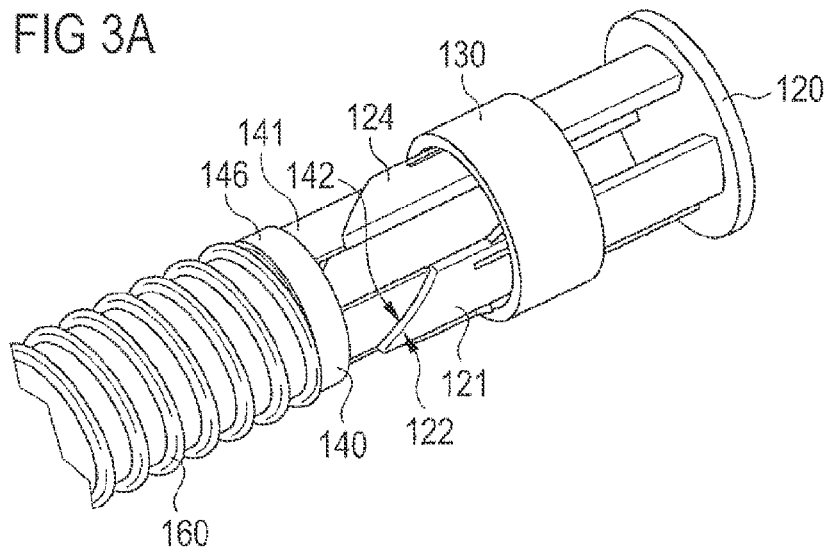
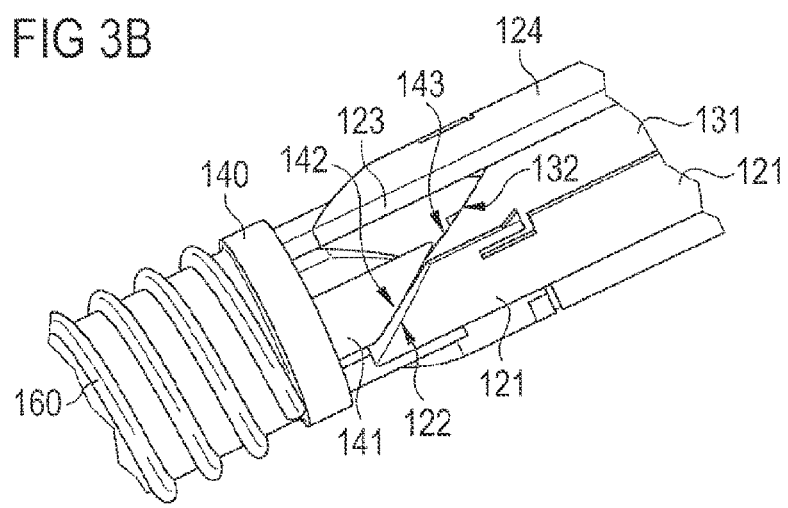
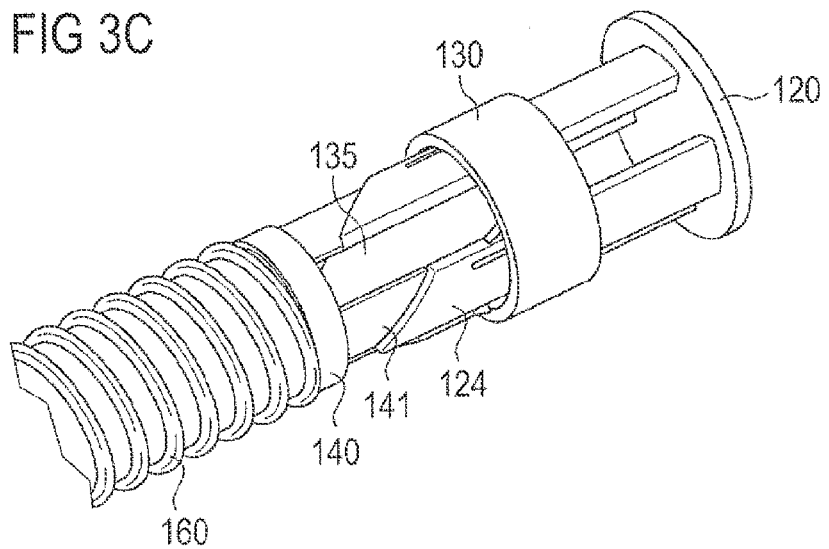

DRIVE ASSEMBLY AND MEDICATION DELIVERY DEVICE

CROSS REFERENCE TO RELATED APPLICATIONS

The present application is a U.S. National Phase Application pursuant to 35 U.S.C. §371 of International Application No. PCT/EP2010/050554 filed Jan. 19, 2010, which claims priority to European Patent Application No. 09000686.7 filed on Jan. 20, 2009. The entire disclosure contents of these applications are herewith incorporated by reference into the present application.

FIELD OF INVENTION

The present invention relates to a drive assembly suitable for a medication delivery device and a medication delivery device.

BACKGROUND

Medication delivery devices may have application where a person without formal medical training needs to administer accurate and/or predefined doses of a medication. In particular, such devices may have an application where medication is administered on a regular or an irregular base over a short term or long term period.

EP 1353712 A1 describes a drive mechanism for an injection device in which a ratchet means is biased by biasing means towards a further ratchet means. A drive means is actuable to drive the further ratchet means. The further ratchet means drives the ratchet means. Thereby biasing means are biased. To drive a piston rod, the ratchet means and the further ratchet means move in an angular direction.

SUMMARY

It is an object of the invention to provide a drive assembly which provides improved operability. It is a further object of the invention to provide a medication delivery device which facilitates a simple and precise delivery of the medication.

This object is achieved by a drive assembly according to claim 1 and a medication delivery device according to claim 15. Advantageous embodiments are subject matter of the dependent claims.

According to a first aspect, a drive assembly suitable for a medication delivery device comprises a housing. The housing comprises a proximal end and a distal end. An axis may run between the proximal end and the distal end. The drive assembly further comprises a drive member. The drive member is axially displaceable with respect to the housing for delivering a dose of medication. The drive assembly comprises a piston rod. The piston rod is rotatable with respect to the housing. The rotation axis of the piston rod lies on the axis which runs between the proximal end and the distal end. The drive assembly further comprises a rotation sleeve. The rotation sleeve is rotatable and axially displaceable with respect to the housing. The drive assembly further comprises a guide member. The guide member has at least one guide track. The guide track extends axially. The rotation sleeve is arranged to releasably engage the at least one guide track. The drive assembly further comprises a biasing member.

The rotation sleeve is arranged to be displaced in the distal direction when the drive member is displaced in the distal direction by mechanical interaction of the drive member and the rotation sleeve. The rotation sleeve and the drive member both are guided axially by the at least one guide track as long as the rotation sleeve engages the at least one guide track. The biasing member is biased during distal movement of the rotation sleeve. The biased biasing member exerts a force on the rotation sleeve acting in the proximal direction. The force is transformed into a rotational movement of the rotation sleeve with respect to the housing. The force is transformed into a proximal movement of the rotation sleeve with respect to the drive member after the rotation sleeve has disengaged the at least one guide track. The rotational movement of the rotation sleeve is transformed into movement of the piston rod with respect to the housing, preferably rotational movement of the piston rod with respect to the housing and/or movement of the piston rod in the distal direction with respect to the housing.

In a further embodiment, the guide member comprises at least one guide finger. The at least one guide finger may limit the at least one guide track in the direction in which the rotation sleeve rotates after the rotation sleeve has disengaged at least one guide track.

In a further embodiment, the rotation sleeve comprises at least one sleeve finger. The at least one sleeve finger may be axially displaceable in and/or along the at least one guide track.

In a further embodiment, the drive member has at least one drive finger. The at least one drive finger may be axially displaceable in and/or along the at least one guide track. The at least one drive finger may be capable of moving the at least one sleeve finger distally within and/or along the at least one guide track.

According to a further embodiment, the at least one guide finger comprises a ramp at its distal end. The at least one drive finger may comprise a ramp at its distal end. The ramp of the at least one drive finger and the ramp of the at least one guide finger are configured to form parts of a rotation ramp together, preferably a continuous rotation ramp. The rotation ramp comprises two pieces. The rotation ramp is formed temporarily. The at least one sleeve finger may slide along the rotation ramp after the at least one sleeve finger leaves the at least one guide track. The at least one sleeve finger may slide along both pieces of the rotation ramp when the at least one sleeve finger leaves the at least one guide track.

According to a further embodiment, the ramp of the at least one drive finger and a ramp of the at least one sleeve finger abut one another during the axial displacement of the rotation sleeve within and/or along the guide track. The at least one guide finger may prevent a rotation of the at least one rotation sleeve as long as the at least one sleeve finger engages the at least one guide track. The rotation sleeve is capable of disengaging the at least one guide track when the ramp of the at least one sleeve finger reaches the distal end of the at least one guide finger. The rotation sleeve may be capable of rotating after having disengaged the at least one guide track. The ramp of the at least one sleeve finger slides along the ramp of the at least one drive finger.

According to a further embodiment, the at least one guide finger is arranged to delimit the rotational movement of the rotation sleeve when the at least one sleeve finger abuts the at least one guide finger. The rotation sleeve and the piston rod may rotate during a displacement of the drive member in the proximal direction with respect to the housing.

According to a further embodiment, the rotation sleeve is configured to reengage the at least one guide track after a disengagement of the rotation sleeve and the guide track.

According to a further embodiment, the rotation sleeve is displaceable with respect to the piston rod in the axial direction. The rotation sleeve may be splined to the piston rod. The piston rod and the rotation sleeve may be engaged such that the piston rod follows the rotational movement of the rotation sleeve. The engagement of the piston rod and the rotation sleeve may or may not have a transmission ratio. The engagement of the piston rod and the rotation sleeve may be configured such that when the rotation sleeve is rotated by a rotation angle the piston rod is rotated a different rotation angle than the rotation sleeve. In another embodiment, the engagement of the piston rod and the rotation sleeve may be configured such that when the rotation sleeve is rotated a rotation angle the piston rod is rotated by the same rotation angle as the rotation sleeve. Rotation sleeve and piston rod are expediently rotated in the same direction.

In a further embodiment, the piston rod and the housing are threadedly engaged. The piston rod may comprise a thread. The thread may comprise at least one first and one second region. The pitch of the at least one first region may be greater than the pitch of the at least one second region. The thread may be faster in the first region than in the second region, i.e. a greater displacement in the distal direction is caused when the first region is passed through a nut member. The housing may comprise a piston rod nut. The piston rod nut may be arranged to be engageable with the thread, in particular with the at least one first region and the at least one second region. The drive assembly is configured such that, when the drive member is moved proximally and the rotation sleeve rotates, the piston rod nut is arranged in the at least one second region.

In a further embodiment, one end of the biasing member is supported on the housing and the other end on the rotation sleeve. The biasing member may comprise a compression spring.

A medication delivery device comprises a drive assembly a described above. The medication delivery device further comprises a medication cartridge. The medication cartridge is expediently coupled to the drive assembly for dispensing the medication.

BRIEF DESCRIPTION OF THE FIGURES

Herein below the embodiments of the invention will be described in more detail in conjunction with the appended drawings.

DETAILED DESCRIPTION

Figure 1:
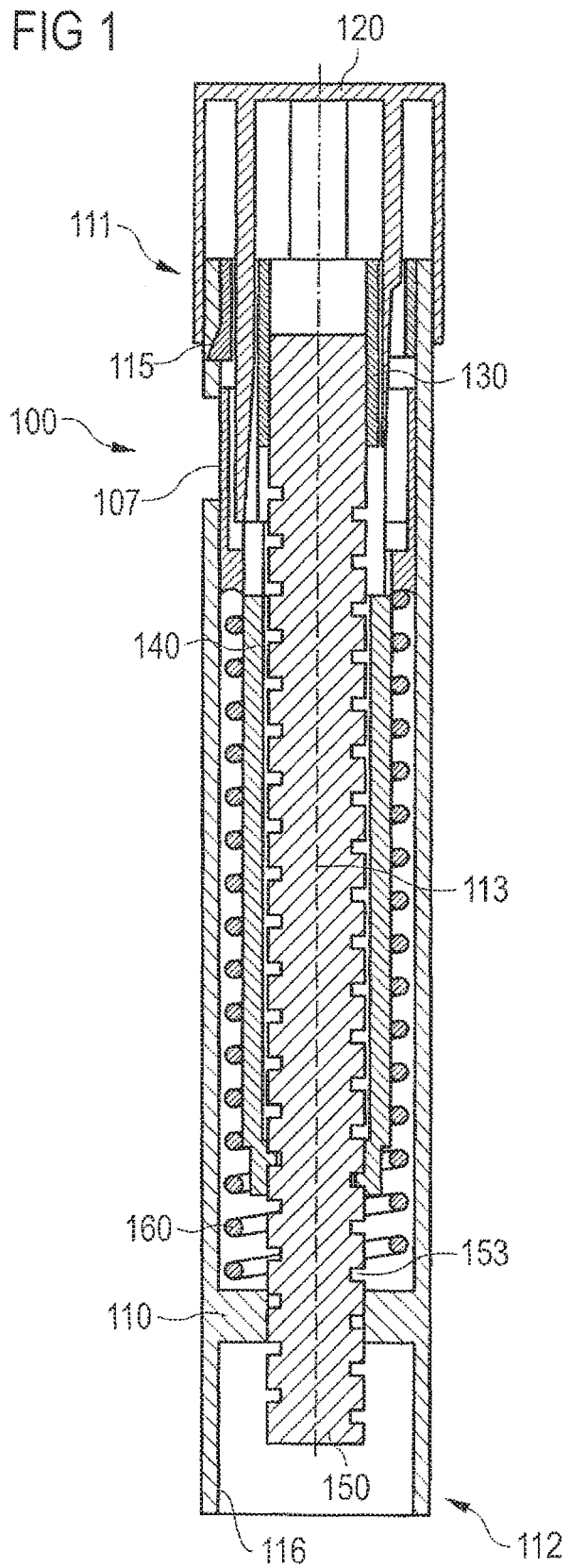
FIG. 1 schematically shows a sectional view of a drive assembly according to an embodiment, FIG. 2 schematically shows a drive finger and a guide member according to an embodiment, FIGS. 3A to 3C schematically show a drive assembly according to an embodiment in different stages of the driving operation of the drive assembly, FIG. 4 schematically shows a housing, a piston rod and a rotation sleeve according to an embodiment, FIG. 5 schematically shows a sectional view of a housing according to an embodiment, FIG. 6 schematically shows a rotation sleeve according to an embodiment, FIG. 7 schematically shows a piston rod according to an embodiment, FIG. 8 schematically shows the run of a thread of a piston rod according to an embodiment, FIG. 9 schematically shows a medication delivery device according to an embodiment.

FIG. 1 shows a drive assembly 100. The drive assembly 100 comprises a housing 110. The drive assembly 100 further comprises a drive member 120. A guide member 130 is comprised by the drive assembly 100. The drive assembly 100 further comprises a rotation sleeve 140. The drive assembly 100 comprises a piston rod 150. The drive assembly 100 further comprises a biasing member 160.

The housing 110 comprises a tubular cylindrical shape, preferably a hollow shape. The housing extends between a proximal end 111 and a distal end 112. The sleeve-like housing 110 may comprise coupling means 115 on the proximal end 111. The housing may comprise coupling means 116 arranged at the distal end 112. The coupling means 116 on the distal end 112 may be for coupling of the housing with a medication cartridge. The housing 110 may comprise further coupling means at the proximal end 111 for coupling further elements of the drive assembly with the housing 110. An axis 113 extends between the proximal end 111 and the distal end 112. The axis 113 basically extends through the center of the housing 110. The inner walls of the housing run along, preferably parallel to and offset from, the axis 113. The axis 113 runs along the longitudinal axis of the housing 110. The housing 110 may comprise an opening 107, for example for displaying information. The information may relate to a medication within the cartridge, like the type of medication or the number of doses of the medication dispensed from and/or remaining in the cartridge.

Figure 2:
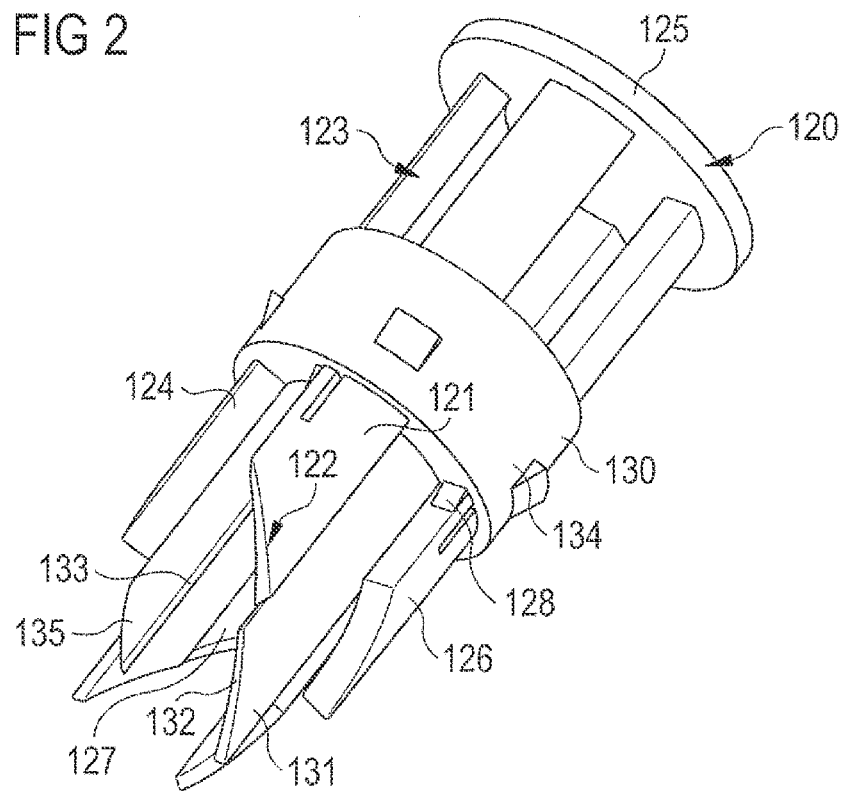

The drive member 120 comprises a base 125 as shown in FIG. 2. The drive member 120 further comprises a plurality of drive fingers, preferably four drive fingers 121, 124, 126, 127. The drive member may also comprise less than four drive fingers, for example three or less drive fingers. In another embodiment the drive member comprises more than four drive fingers, for example five or more drive fingers.

The drive fingers 121, 124, 126, 127 are fixed to the base 125 or may be integrated in the base. The base and the drive fingers may be manufactured as one single piece. In another embodiment the base and the drive fingers may be assembled out of different parts. The drive fingers 121, 124, 126, 127 preferably are equidistantly arranged on the base 125. The drive fingers 121, 124, 126, 127 are arranged around the axis 113. The drive fingers 121, 124, 126, 127 may surround a hollow inside of the drive fingers.

The drive fingers 121, 124, 126, 127 each comprise a first part which runs along, basically parallel, to the axis 113 (this part is shown in FIG. 1). The drive fingers each comprise an edge 123 which runs along the first part of the drive fingers basically parallel to the axis 113. At the respective ends of the drive fingers opposite to the base 125 each drive finger comprises a ramp 122. Each drive finger comprises the respective ramp 122 at its distal end.

The respective ramps 122 are oblique with respect to the edge 123. In a projection onto a plane that comprises the axis 113, the ramp 122 runs obliquely with respect to the axis 113. In a projection onto a plane that comprises the axis 113, the ramp 122 runs not perpendicular with respect to the axis 113. The angles of the ramps in the distal direction of all of the drive fingers are basically equal, preferably approximately 45°. The respective angle is preferably at least as great such as to avoid a self-locking of the drive member 120 and the rotation sleeve 140. In another embodiment the angles in the distal direction of different drive fingers are different from each other. With respect to the respective rectilinear parts, the respective ramps 122 are oriented in the same direction. The drive fingers each comprise a rectilinear part which runs from the ramps towards the proximal end of the respective drive finger. The respective rectilinear part runs from the ramp 122 to the base 125. The respective ramp extends from one edge of the drive finger to the opposite edge of the same drive finger.

The drive member 120 may comprise coupling means for coupling the drive member 120 with further elements. For example, a dose button (not shown) may be coupled to the drive member 120. The dose button may be pushed in distal direction with respect to the housing for administering a dose of medication. The dose button may transfer a force exerted on the dose button in distal direction to the drive member 120. In another embodiment the force for administering a dose of medication is exerted directly on the drive member 120. In this embodiment no separate dose button is needed. The force may be a force exerted manually on the dose button by a user.

The guide member 130 as shown in FIG. 2 comprises a base 134. The base 134 comprises a ring-like shape. The base 134 may define a hollow inside. The base 134 is cylindrically shaped and basically surrounds the axis 113. The guide member 130 further comprises a plurality of guide fingers 131, preferably four guide fingers 131. The guide member may comprise less than four guide fingers, for example three or less guide fingers. The guide member may also comprise more than four guide fingers, for example five or more guide fingers.

The guide member 130 comprises a sleeve-like shape. The guide fingers 131 are arranged on one side of the base 134, for example the distal side. The guide fingers 131 are distributed around the base 134, preferably equidistantly spaced on the base 134.

Each of the guide fingers 131 comprises an elongate rectilinear part which may start at the base 134. The rectilinear part may extend along the axis 113, in particular basically parallel to the axis 113. At the end opposite to the base 134 each of the guide fingers comprises a ramp 132. At the distal end each of the guide fingers comprises the respective ramp 132. The ramp is oblique with respect to the axis 113 in a projection onto a plane that comprises the axis 113. The ramp 132 runs not perpendicular with respect to the axis 113. The angle of all of the oblique ramps 132 of the drive fingers 131 is basically equal in the distal direction, preferably approximately 45°. In another embodiment the angles in the distal direction of different ramps may differ from each other. With respect to the respective rectilinear parts, the respective ramps 132 are directed in the same direction. In the distal direction, the ramps 132 are directed in the same direction as the ramps 122 of the drive member 120.

The guide member 130 has a respective guide track 133 adjacent to each of the guide fingers 131. The guide tracks extend along the guide fingers 131 and along the axis 113, preferably basically parallel to the axis 113. The guide tracks 133 extend along the longer side of each of the respective guide fingers 131. The guide tracks 133 are limited by the respective guide fingers 131. Two adjacent guide fingers form one guide track between each other, respectively.

The rotation sleeve 140 comprises a base 146 as shown in FIGS. 3A to 3C. The base 146 comprises a tubular cylindrical shape. The base 146 extends along the axis 113, preferably basically parallel to the axis 113. The rotation sleeve 140 surrounds the axis 113. At a proximal end of the rotation sleeve a plurality of sleeve fingers 141 is arranged, for example four sleeve fingers 141 are arranged. The rotation sleeve may comprise less than four sleeve fingers, for example three or less sleeve fingers. In another embodiment the rotation sleeve comprises more than four sleeve fingers, for example five or more sleeve fingers.

The sleeve fingers 141 extend proximally along the axis 113, preferably starting at the base 146. The sleeve fingers extend along the axis 113, preferably basically parallel to the axis 113. The sleeve fingers preferably are equidistantly spaced on the base 146. The sleeve fingers are arranged around the axis 113. The sleeve fingers 141 surround a hollow inside of the sleeve fingers. At the proximal end of each of the sleeve fingers a ramp 142 is formed. The ramps 142 respectively are formed on the end of the sleeve fingers opposite to the base 146.

The sleeve fingers each comprise a rectilinear part which runs from the ramps in the proximal direction, in particular towards the proximal end of the respective sleeve finger. The respective rectilinear parts run from the ramps 142 to the base 146. The rectilinear part may extend along the axis 113, basically parallel to the axis 113. In a projection onto a plane that comprises the axis 113, the ramps 142 are oblique with respect to the axis 113. The ramps 142 run not perpendicular with respect to the axis 113. The direction of the oblique ramps 142 is in opposition to the direction of the ramps 122 of the drive fingers in the distal direction. The orientation of the ramps 142 is opposite to the orientation of the ramps 132 of the guide fingers 131 in the distal direction. The angles of the respective ramps 142 are basically equal in the distal direction, preferably approximately 45°. In another embodiment the angles in the distal direction of the different ramps may differ from each other. With respect to the respective rectilinear parts, the respective ramps 142 are directed in the same direction.

The piston rod 150 comprises a cylindrical shape. The piston rod is oriented basically along the axis 113. The piston rod comprises a thread 153. The tread 153 extends partly along the outer surface of the piston rod 150. In another embodiment the thread extends along the total outer surface of the piston rod. At the distal end, the piston rod 150 may comprise coupling means for coupling the piston rod 150 with a plunger (not shown). The piston rod may comprise a thread which comprises two or more than two different regions. Different regions of the thread may succeed one another in a regular or irregular pattern along the course of the thread. The further regions may comprise further pitches which are different from each other. The thread is interrupted by at least one, preferably two, guide slots. The guide slots are for guiding the rotation sleeve. The guide slots extend along the axis 113.

Figure 8:
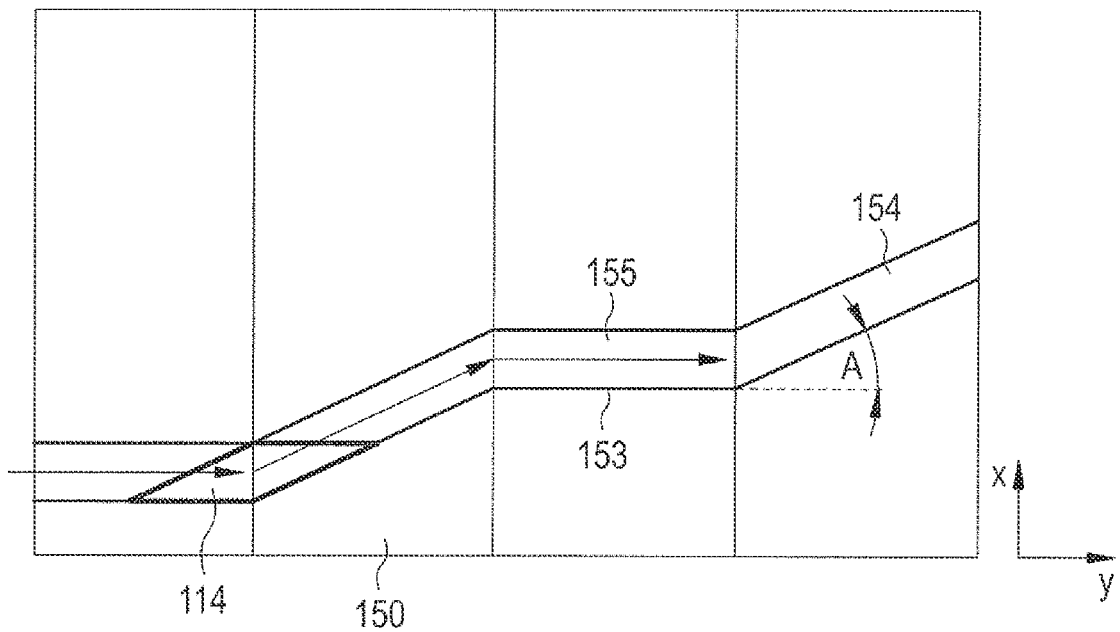

As shown in FIG. 8 the thread 153 comprises a first region 154. The vertical lines are parallel to the axis 113. The thread comprises a second region 155. The two regions 154 and 155 merge into each other. One first region 154 is arranged between two second regions 155. One second region 155 is arranged between two first regions 154. The first region 154 and the second region 155 may be arranged in alternating fashion along the course of the thread 153.

The first region 154 comprises a pitch which is different from the pitch of the second region 155. The pitch of the second region 155 is smaller than the pitch of the first region 154. According to the embodiment shown in FIG. 8 the region 155 is flat in the projection plane with respect to the axis 113. In the shown projection of the thread the second region 155 runs transversely, preferably perpendicularly, to the axis 113. The first region 154 comprises an angle different from 90° with respect to the axis 113. The region 154 expediently includes an angle with the axis 113, in projection, which is smaller than the angle, the region 4 includes with the axis.

The biasing member 160 comprises a helical compression spring. One end of the biasing member is supported by the housing 110 on an inwardly protruding portion thereof. The opposed end of the biasing member 160 is supported on the rotation sleeve 140 on the distal side. The biasing member 160 is supported on a flange portion of the rotation sleeve 140. As shown in FIG. 3, the biasing member 160 is supported on the base 146 of the rotation sleeve 140. Alternative or in addition, the biasing member may comprise other elements, for example a leave spring or an elastomer.

As shown in FIG. 2 the drive member 120 and the guide member 130 are coupled. The guide member 130 permanently secures the drive member 120 against rotation with respect to the guide member 130. The drive member 120 is linearly movable along the axis 114 with respect to the guide member 130. The drive fingers 121, 124, 126, 127 run in respective guide tracks 133. The drive member 120 and the guide member 130 are displaceable with respect to each other along the axis 113. The guide tracks 133 prevent a rotational movement of the drive member 120 and the guide member 130 with respect to each other.

The guide fingers 131 prevent a rotational movement of the drive member 120 and the guide member 130 with respect to each other. Due to the arrangement of the guide fingers 131 with respect to the drive fingers 120 only an axial displacement of the drive member 120 with respect to the guide member 130 is enabled. In another embodiment the guide member 130 comprises further guide tracks in which the drive fingers are arranged such that the drive fingers can abut the sleeve fingers.

A stop member 128 is arranged at each of the drive fingers 121, 124, 126, 127 respectively. The stop members 128 limit the proximal movement of the drive member 120 with respect to the guide member 130. When the stop members 128 abut the base 134 of the guide member 130 further proximal movement of the drive member 120 with respect to the guide member 130 is restricted.

FIG. 3A shows a starting position of elements of the drive assembly before a dose of a medication is administered. The drive member 120, the guide member 130 and the rotation sleeve 140 are coupled. The biasing member 160 may exert a force on the rotation sleeve 140 which keeps the rotation sleeve 140 in contact with the drive member 120. The sleeve fingers 141 abut the drive fingers 121, 124, 126, 127. The ramps of the drive fingers abut the ramps of the sleeve fingers. One drive finger and one associated sleeve finger are arranged in a common guide track. The guide member 130 is secured against a displacement with respect to the housing 110. The guide member 130 is secured to the housing 110 by fixing means, for example snap-fitted fixing means. The guide member 130 can not rotate with respect to the housing 110. The guide member 130 can not be displaced along the axis 113 with respect to the housing 110. The guide member permanently secures the drive member 120 against rotation with respect to the housing 113.

For administering medication, the drive member 120 is displaced in the distal direction with respect to the housing. The drive fingers 121, 124, 126, 127 are secured against a rotational movement with respect to the guide member 130. The drive fingers are displaced axially. Due to the movement of the drive member 120 and correspondingly the drive fingers 121, 124, 126, 127, the rotation sleeve 140 is displaced in the distal direction. The sleeve fingers 141 are secured against rotation with respect to the guide member 130 by the guide fingers. The guide fingers prevent a rotation of the rotation sleeve 140 with respect to the guide member 130 as long as the sleeve fingers run within the guide tracks.

Due to the mechanical contact of the drive member 120 and the rotation sleeve 140 via the ramps 142 and 122 a tangential force is applied on the rotation sleeve in the rotation direction. The sleeve fingers are pressed against the guide fingers in a direction transverse to the direction of the displacement. The sleeve fingers may slide along the guide fingers. The rotation sleeve 140 does not rotate with respect to the drive member 120 as long as the sleeve fingers are arranged in the guide tracks. The rotation sleeve 140 does not rotate with respect to the guide member 130 as long as the sleeve fingers are arranged in the guide tracks. The rotation sleeve 140 does not rotate with respect to the housing 110 as long as the sleeve fingers are arranged in the guide tracks.

The guide member 130 is fixed to the housing 110 and secured against a movement with respect to the housing 110. The drive member 120 is axially displaced with respect to the housing 110 and thereby axially displaces the rotation sleeve 140. The guide member 130 axially guides the rotation sleeve 140. The sleeve fingers 141 slide along the guide fingers 131 of the guide member 130. Due to the distal displacement of the rotation sleeve 140, the biasing member 160 is biased.

In FIG. 3B, the drive member 120 is moved further on in the distal direction in comparison with FIG. 3A. The drive member 120 is moved distally with respect to the guide member 130 until the ramp 122 of the drive finger 121 forms a continuous rotation ramp 143 together with the ramp 132 of the guide finger 131. Then, the sleeve fingers have disengaged the guide tracks. The sleeve fingers disengage from all of the guide tracks. The drive member preferably stops in this position, e.g. by abutting a distal end stop (not shown). After the sleeve fingers 141 have disengaged the guide tracks, the rotation sleeve 140 is capable of rotation with respect to the guide member 130.

The ramp 142 slides along the ramp 122 and along the ramp 132. The rotation sleeve 140 rotates until the sleeve finger 141 abuts the drive finger 124. The drive finger 124 prevents a further rotational movement of the rotation sleeve 140 with respect to the guide member 130 as long as the sleeve finger 141 abuts the edge 123 of the drive finger 124.

The rotational movement during the sliding along the ramp 122 of the rotation sleeve 140 is caused by the force the biasing member 160, which was previously biased, exerts in the proximal direction. The biasing member may relax (partly) in the proximal direction. The biasing member 160 presses the oblique ramp 142 of the sleeve finger 141 against the oblique rotation ramp 143. Since the rotation ramp 143 and the ramp 142 comprise a matching pitch, the force of the biasing member 160 is transferred into a rotational movement of the rotation sleeve 140 with respect to the guide member 130. The rotation sleeve 140 also rotates with respect to the housing 110. The rotation sleeve also rotates with respect to the drive member 120. The rotation sleeve 140 is proximally displaced with respect to the drive member 120, the guide member 130 and the housing 110. The rotation sleeve 140 performs a movement until it abuts a stop member which can be moved away from sleeve fingers and which can be decoupled from the sleeve fingers, for example the rotation sleeve 140 performs a movement until it abuts the (next) drive finger 124.

When the drive member 120 is displaced proximally so far that the ramp of the drive finger 124 continues the ramp 132 of the guide finger 131, the ramp 142 may slide along the ramp of the drive finger 124. Due to the sliding the rotation sleeve 140 rotates with respect to the guide member 130. The rotation is stopped by the sleeve finger 141 abutting the guide finger 135. The sleeve finger 141 and the drive finger 124 may be displaced axially in the guide track formed by means of the guide finger 135, in particular in the proximal direction with respect to the housing. The displacement may be caused by the force exerted by the biasing member 160. The biased biasing member 160 may relax in the proximal direction, thereby moving the rotation sleeve in the proximal direction with respect to the housing.

The sliding of the sleeve finger 141 along the rotation ramp 143 which is formed by the ramp of the drive finger 121 and the guide finger 131 is stopped by the drive finger 124. The rotation sleeve 140 rotates with respect to the drive sleeve 120 and with respect to the guide member 130 until the sleeve finger 141 abuts the drive finger 124. During a further proximal movement of the drive member 120 the rotation sleeve 140 is secured against a rotational movement due to the lateral engagement of the sleeve finger 141 and the drive finger 124.

During a further proximal movement of the drive member 120, the distal end of the drive finger 124 is reached and the rotation sleeve 140 is free to rotate a further section. The rotation is caused by a sliding of the ramp 142 of the sleeve finger 141 on the ramp drive finger 124. During the rotation, the rotation sleeve 140 is proximally displaced. The rotation of the rotation sleeve 140 is stopped by a guide finger 135.

The rotation finger 141 engages the guide track formed by the guide finger 135. This state is shown in FIG. 3C. The drive member 120 is displaced proximally with respect to the guide member 130 in comparison with FIG. 3B. Due to the displacement of the drive fingers, in particular the drive finger 124, the rotation sleeve 140 rotates further with respect to the guide member 130 until the sleeve finger 141 abuts the guide finger 135.

During a further proximal movement of the drive member 120 the rotation sleeve 140 is axially displaced and so is the drive member 120. Due to the guide track of the guide finger 135 the rotation sleeve 140 is secured against rotation during the proximal movement of the drive member 120. The rotation sleeve 140 and the drive member 120 can be displaced proximally with respect to the guide member 130 until the home position is reached. The home position may be determined by a proximal end stop which may limit proximal movement of the drive member.

Figure 4:
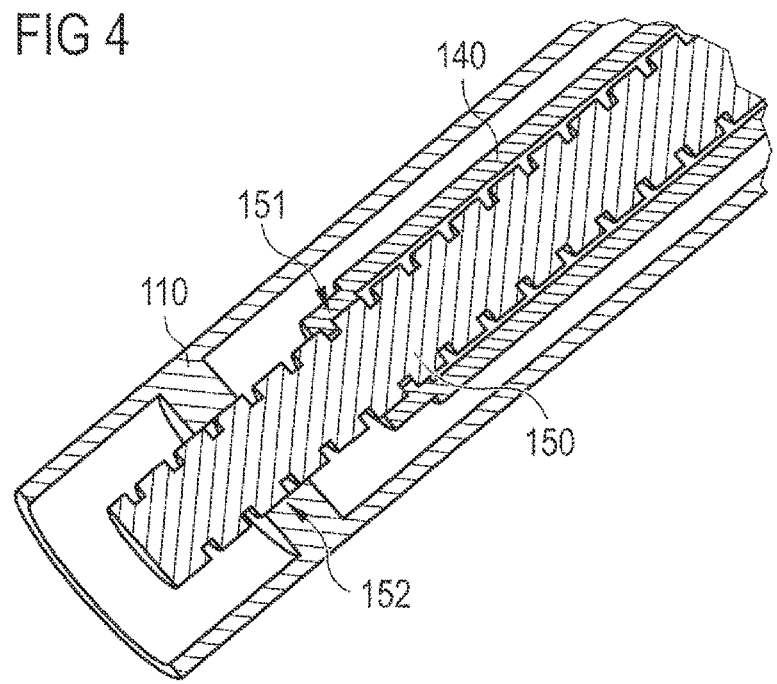

FIG. 4 shows a coupling 151 of the rotation sleeve 140 and the piston rod 150. FIG. 4 further shows a coupling 152 of the housing 110 and the piston rod 150.

The piston rod 150 and the rotation sleeve 140 are engaged such that a rotational movement of the rotation sleeve 140 with respect to the housing 110 results in a rotational movement of the piston rod 150 with respect to the housing 110. The piston rod 150 and the rotation sleeve 140 may be splined. An axial displacement of the rotation sleeve 140 with respect to the piston rod 150 does not cause a movement of the piston rod 150. During a linear movement of the rotation sleeve 140 the coupling 151 slides along the piston rod 150. During a rotational movement of the rotation sleeve the coupling 151 may engage the piston rod, such that a rotation of the rotation sleeve is transformed into a rotation of the piston rod 150 of the same angle, e.g. by the coupling abutting the piston rod. The rotation sleeve 140 preferably engages linear guide slots of the piston rod 150 with engaging members of the piston rod that may be provided arranged on an inner surface of the rotation sleeve.

Figure 5:
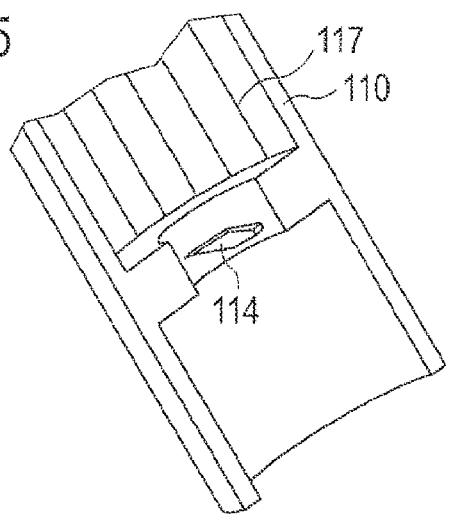

To displace the rotating piston rod 150 distally with respect to the housing 110, the housing and the piston rod are threadedly engaged at the coupling 152. The housing 110 comprises a piston rod nut 114 as shown in FIG. 5. The pitch of the thread of the piston rod 150 and the piston rod nut 114 determine the linear displacement of the piston rod when the piston rod is rotated with respect to the housing 110.

The thread of the piston rod 150 comprises different pitches. Due to the different pitches, a rotational movement of the piston rod 150 results in different linear displacements of the piston rod with respect to the housing. The distance of the linear displacement is dependent on the pitch of the part of the thread which is passed through the piston rod nut 114 while the piston rod rotates for being displaced. The thread 153 of the piston rod 150 is configured to prevent a distal movement of the piston rod 150 when the drive member 120 is moved proximally towards the starting position. Consequently, rotational movement of the rotation sleeve when the drive member is moved proximally is preferably not converted into distal movement of the piston rod. The thread is configured and, in operation, coordinated with the piston rod nut 114 such that during a displacement of the drive member in the proximal direction and a (simultaneous) rotation of the piston rod with respect to the housing, the piston rod is not displaced in the distal direction with respect to the housing.

The axis 113 is the rotation axis of the piston rod 150. The axis 113 is the rotation axis of the rotation sleeve 140.

FIG. 5 shows a sectional view of the housing 110. The piston rod nut 114 which can engage with the thread 153 of the piston rod 150 comprises a parallelogram-like shape. The piston rod nut 114 is shaped, such that the piston rod nut 114 can slide through the different pitches of the thread 153 of the piston rod 150. The piston rod nut 114 does not block within the thread 153 of the piston rod 150. The piston rod 150 and the housing 110, in particular the thread 153 and the piston rod nut 114 form a non-self-locking thread connection. The piston rod nut 114 may be integrated in the housing 110 or may be a separate piece which is fixed to the housing.

Figure 6:
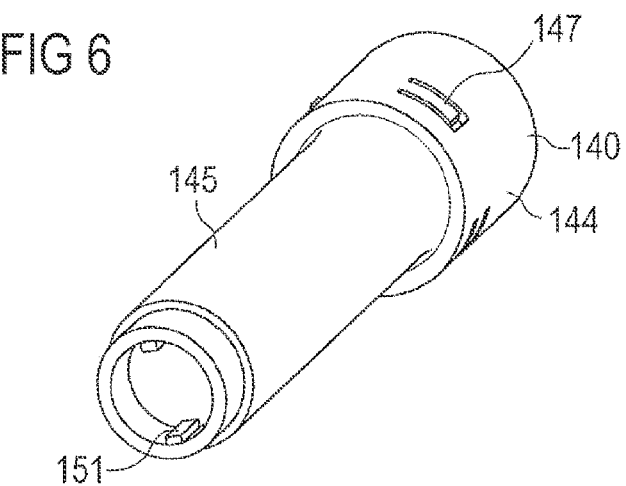

FIG. 6 shows rotation sleeve 140. The rotation sleeve comprises a first part 144 and a second part 145. The rotation sleeve surrounds a hollow inside. A piston rod can be arranged inside the rotation sleeve 140. At an end of the rotation sleeve 140 adjacent to the second part 145 coupling means for the coupling 151 are arranged. A cross-section of the second part 145 is smaller than a cross-section of the first part 144. The first part 144 is adjacent to the proximal end of the rotation sleeve 140. The second part 145 is adjacent to the distal end of the rotation sleeve 140. The biasing member 160 can be supported on the nose or flange formed by the first part 144. At the first part 144 sleeve fingers 141 are arranged (not explicitly shown). The first part 144 is configured to couple the rotation sleeve 140 with the housing 110.

At least one feedback member 147 is arranged at the first part 144 of the rotation sleeve 140. The feedback member 147 is biased outwards with respect to the rotation sleeve 140. The feedback member is preferably a resilient member. To realize a tactile and/or audible feedback the feedback member 147 interacts with at least one spline 117 of the housing 110 (shown in FIG. 5). When the rotation sleeve 140 is rotated with respect to the housing 110 the feedback member abuts the spline 117 and thereby creates the tactile and/or audible feedback. The tactile and/or audible feedback may give a user information about the end of injection operation and/or the setting of dose.

Figure 7:
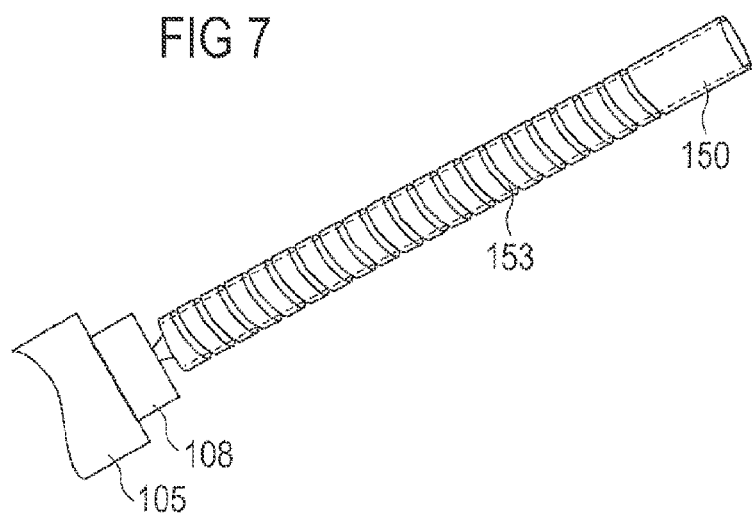

FIG. 7 shows the piston rod 150. The piston rod 150 is partly threaded. The thread 153 extends from the distal end of the piston rod 150 towards the proximal end. A part of the piston rod 150 adjacent to the proximal end is not threaded. In another embodiment the thread extends all the way from the distal end to the proximal end.

The thread of the piston rod comprises different pitches. In combination with the housing 110, a rotation of the piston 150 with respect to the housing is transformed into a linear movement of the piston rod 150 with respect to the housing 110. The transmission ratio is set by the pitch of the thread 153. A pitch which rises more steeply results in a greater linear displacement of the piston rod 150. A pitch which rises less steeply results in lesser linear displacement of the piston rod 150. A pitch of the thread 153 which is basically perpendicular to the rotation axis of the piston rod 150 results in no linear displacement of the piston rod 150 with respect to the housing 110 when engaged by the piston rod nut 114 during operation.

The piston rod 150 comprises means for a coupling with the rotation sleeve 140. The piston rod 150 follows a rotational movement of the rotation sleeve 140 while a linear displacement of the rotation sleeve 140 with respect to the piston rod 150 possible without a displacement of the piston rod 150.

The piston rod 150 may abut a plunger 105. A bearing member 108 may be arranged between the piston rod 150 and the plunger 105. A displacement of the plunger 105 in the distal direction leads to a dispensing of medication. A distal end face of the piston rod 150 may be arranged to abut a proximal end face of the plunger 105. A bearing member 108 may be arranged to advance the plunger 105, preferably to abut the proximal end face of the plunger 105. The bearing member may be fixed to the piston rod 150 or a separate member.

When the piston rod 150 is configured to be rotated during operation of the device, for example during dose delivery, it is particularly expedient to provide for a bearing member. The bearing member may be displaced together with the (rotating) piston rod with respect to the housing. The piston rod may be rotatable with respect to the bearing member. In this way, the risk that the rotating piston rod drills into the piston and thereby damages the piston is reduced. Accordingly, while the piston rotates and is displaced with respect to the housing, the bearing member is preferably only displaced, i.e. does not rotate. The piston rod may be bounded by the bearing member.

FIG. 8 schematically shows the course of the thread 153. The piston rod nut 114 is schematically shown. The X-axis runs parallel to axis 113 and the Y-axis runs perpendicularly to the X-axis.

The part 155 of the thread 153 extends basically perpendicularly to the X-axis. When the piston rod nut 114 runs along the part 155, i.e. the piston rotates such that the part 155 passes the piston rod nut 114, the piston is not displaced along the X-axis with respect to the piston rod nut 114. When the piston is further rotated the piston rod nut 114 enters the part 154. The part 154 comprises an angle A with respect to the X-axis. When the piston rod nut 114 runs along the part 154, the piston rod 150 is displaced with respect to the piston rod nut 114 along the X-axis. The distance of the displacement along the X-axis is defined by the pitch of the part 154.

Due to the shape of the piston rod nut 114, the piston rod nut can slide along the part 155 and also along the part 154. The piston rod nut 114 may comprise a parallelogram-like shape. The piston rod nut 114 may comprise a rhombic shape. Two opposite surfaces of the piston rod nut 114 may run along, in particular basically parallel, to the pitch of the part 155. The other two opposite surfaces of the piston rod nut 114 may run along, in particular basically parallel, to the flanks of part 154. Hence, a movement of the piston rod with respect to the piston rod nut in part 154 as well as in part 155 is facilitated. In operation, during dispensing of a dose of medication, the piston rod nut 114 runs in the part 154, preferably, thereby causing distal displacement of the piston rod with respect to the housing. In operation, while no medication should be dispensed, the piston rod nut 114 runs in the part 155, preferably, thereby causing no distal displacement of the piston rod with respect to the housing.

Figure 9:
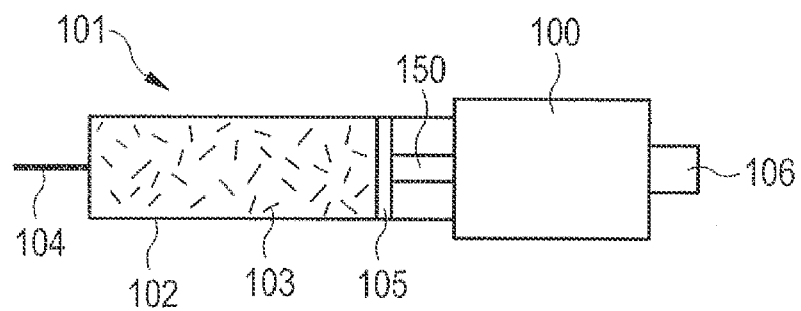

FIG. 9 shows a medication delivery device 101. The medication delivery device 101 may be a fixed dose device, in particular a device for dispensing fixed, non user-settable, for example constant, doses. The medication delivery device comprises a medication cartridge 102. The medication cartridge holds medication 103. The medication delivery device 101 further comprises a needle device 104. The needle device 104 is arranged at the distal end of the medication cartridge 102 and is preferably secured to it. The medication 103 can be dispensed through the needle device 104. The medication 103 may comprise insulin, growth hormones, low molecular weight heparins, and/or their analogues and/or derivatives. The medication 103 may be fluid.

The plunger 105 is arranged inside the cartridge 102. The plunger 105 is capable of being displaced inside the cartridge 102. A displacement of the plunger 105 in the distal direction leads to a dispensing of medication. The plunger 105 is actuated by the piston rod 150. The piston rod is coupled to the plunger 105. The bearing member may be arranged between the piston rod 150 and the plunger 105.

At the proximal end of the cartridge 102, the drive assembly 100 is arranged. The cartridge may be secured to the housing 110 at the distal end side of the housing 110. An actuation of a dose button 106, preferably a manually actuated movement of the dose button with respect to the housing, causes linear displacement of the drive member which is part of the drive assembly 100. The drive member is linearly displaced in the distal direction, for example towards the distal end, and the needle device 104 respectively. The distal displacement of the drive member causes distal displacement of the rotation sleeve. The distal displacement of the rotation sleeve is a linear displacement.

The linear distal displacement of the rotation sleeve biases a biasing member. During this movement the piston rod 150 keeps its position with respect to the housing. When the dose button 106 is completely pushed up to a distal end stop, the rotation sleeve is free to rotate with respect to the housing and the drive member. The rotation of the rotation sleeve is caused by the force of the biased biasing member.

The rotation sleeve is also moved proximally, in particular while it is rotating. During a first displacement of the rotation sleeve in the proximal direction, the rotation sleeve rotates. This rotation causes rotation of the piston rod with respect to the housing. Due to the threaded coupling, the piston rod is displaced in the distal direction. Due to the movement of the piston rod in the distal direction, the plunger 105 is displaced in the distal direction and thereby medication is dispensed through the needle device 104. The rotation sleeve rotates until it abuts a removable stop member, for example the drive member, in particular one or more of the drive fingers thereof. The amount of dispended medication is determined by the linear displacement of the plunger and the piston rod and thus dependents of the pitch of the thread of the piston rod.

After releasing the dose button 106, the dose button 106 moves proximally with respect to the drive assembly 100 towards and in particular into its starting position. During this proximal displacement the drive member moves also in a proximal direction with respect to the housing. After a certain proximal displacement of the drive member the stop member is thereby removed and the rotation sleeve is free to rotate a further distance. During this rotation when the drive member is proximally displaced, the piston rod rotates, but, preferably, due to the configuration of the thread it is not displaced linearly with respect to the drive assembly 100. Preferably, during this rotation, no medication is dispensed.

During a movement of the dose button in the proximal direction no medication is dispensed preferably. Thereby the risk of a wrongly administered dose is reduced.

To fully reach the starting position, the dose button 106 and the drive member 120 further move proximally. The rotation sleeve follows the drive member and moves linearly in the proximal direction towards its starting position. The movement of the drive member and the rotation sleeve is guided by the guide member. During the whole movement for the dispensing of a dose of medication and back into the starting position, the drive member is guided by two different guide tracks. To dispense a further dose of medication the usage of the drive assembly as described is repeated.

The device may be of any shape, e.g. compact or pen-type. Furthermore, the said device may be needle-free. In particular, the medication delivery device may be a disposable needle-based pen-type device providing multiple predefined doses. The medication delivery device is designed for use by persons without formal medical training.

The device may comprise further elements (not shown), for example sensors and/or electronic circuits. The device may comprise an electronic actuator (not shown) and/or a display for providing information to the user. The information may comprise information about the number of doses of medication and/or the number of doses dispensed from a given cartridge and/or the number of doses remaining in a given cartridge.

The term "housing" shall preferably mean any exterior housing ("main housing", "body", "shell") or interior housing ("insert", "inner body"), which preferably has a unidirectional axial coupling to prevent proximal movement of specific components. The housing may be designed to enable the safe, correct, and comfortable handling of the medication delivery device or any of its mechanisms. Usually, it is designed to house, fix, protect, guide, and/or engage with any of the inner components of the medication delivery device (e.g., the drive assembly, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may be dispensed.

The term "piston rod" shall preferably mean a component adapted to operate through/within the housing, designed to transfer axial movement through/within the medication delivery device, preferably from the drive member to the piston or plunger, preferably for the purpose of discharging/dispensing an injectable product. The piston rod may be flexible or not. It may be a simple rod, a lead-screw, a rack and pinion system, a worm gear system, or the like. The term "piston rod" shall preferably further mean a component having a circular or non-circular cross-section. It may be made of any suitable material known by a person skilled in the art and may be of unitary or multipart construction.

The "distal end" of the device or a component of the device shall mean the end, which is closest to the dispensing end of the device.

The "proximal end" of the device or a component of the device shall mean the end, which is furthest away from the dispensing end of the device.

The invention claimed is:

1. A drive assembly suitable for a medication delivery device, the drive assembly comprising:
    a housing having a proximal end and a distal end, an axis running between the proximal end and the distal end;
    a drive member being axially displaceable with respect to the housing for delivering a dose of a medication;
    a piston rod which is rotatable with respect to the housing;
    a rotation sleeve which is rotatable and axially displaceable with respect to the housing;
    a guide member having at least one guide track extending axially, the rotation sleeve being arranged to releasably engage the at least one guide track; and
    a biasing member, wherein
    the rotation sleeve is arranged to be displaced in the distal direction when the drive member is displaced in the distal direction by mechanical interaction of the drive member and the rotation sleeve with the rotation sleeve and the drive member both being guided axially by the at least one guide track as long as the rotation sleeve engages the at least one guide track, and wherein
    the biasing member is biased during distal movement of the rotation sleeve, the biased biasing member exerts a force on the rotation sleeve acting in the proximal direction, said force being transformed into a rotational movement of the rotation sleeve with respect to the housing and a proximal movement of the rotation sleeve with respect to the drive member after the rotation sleeve has disengaged the at least one guide track, the rotational movement of the rotation sleeve being transformed into a rotational movement of the piston rod with respect to the housing.

2. The drive assembly according to claim 1, wherein the guide member comprises at least one guide finger, the at least one guide finger limits the at least one guide track in the direction in which the rotation sleeve rotates after the rotation sleeve has disengaged the at least one guide track.

3. The drive assembly according to claim 2, wherein the rotation sleeve comprises at least one sleeve finger, the at least one sleeve finger being axially displaceable in the at least one guide track.

4. The drive assembly according to claim 3, wherein the drive member has at least one drive finger, the at least one drive finger being axially displaceable in the at least one guide track and wherein the at least one drive finger is capable of moving the at least one sleeve finger distally within the at least one guide track.

5. The drive assembly according to claim 4, wherein:
    the at least one guide finger comprises a ramp at its distal end,
    the at least one drive finger comprises a ramp at its distal end, and wherein
    the ramp of the at least one drive finger and the ramp of the at least one guide finger are configured to temporarily form parts of a continuous rotation ramp together, such that the at least one sleeve finger slides along the rotation ramp after the at least one sleeve finger leaves the at least one guide track.

6. The drive assembly according to claim 5, wherein:
    the ramp of the at least one drive finger and a ramp of the at least one sleeve finger abut one another during the axial displacement of the rotation sleeve within the guide track,
    the at least one guide finger prevents a rotation of the at least one rotation sleeve as long as the at least one sleeve finger is arranged in the at least one guide track,
    the rotation sleeve is capable of disengaging the at least one guide track when the ramp of the at least one sleeve finger reaches the distal end of the at least one guide finger,
    the rotation sleeve is capable of rotating after having disengaged the at least one guide track with the ramp of the at least one sleeve finger sliding along the ramp of the at least one drive finger.

7. The drive assembly according to claim 2, wherein the rotation sleeve is configured to reengage the at least one guide track after a disengagement of rotation sleeve and the guide track.

8. The drive assembly according to claim 1, wherein during a displacement of the drive member in the proximal direction with respect to the housing, the rotation sleeve and the piston rod rotate.

9. The drive assembly according to claim 1, wherein the rotation sleeve is displaceable with respect to the piston rod in the axial direction.

10. The drive assembly according to claim 1, wherein the piston rod and the rotation sleeve are engaged such that the piston rod follows the rotational movement of the rotation sleeve.

11. The drive assembly according to claim 1, wherein the piston rod and the housing are threadedly engaged.

12. The drive assembly according to claim 1, wherein:
   the piston rod comprises a thread, the thread comprising at least one first and one second region, the pitch of the at least one first region is greater than the pitch of the at least one second region,
   the housing comprises a piston rod nut which is arranged to be engaged with the at least one first region and the at least one second region, and
   the drive assembly is configured such that, when the drive member is moved proximally and the rotation sleeve rotates, the piston rod nut engages the at least one second region.

13. The drive assembly according to claim 1, wherein one end of the biasing member is supported on the housing and the other end on the rotation sleeve.

14. The drive assembly according to claim 1, wherein the biasing member comprises a compression spring.

15. A medication delivery device, comprising:
   a drive assembly according to any of claims 1 to 14,
   a medication cartridge, the medication cartridge being coupled to the drive assembly so as to dispense the medication.

\* \* \* \* \*